(12) United States Patent
Werner et al.

(10) Patent No.: US 9,149,215 B2
(45) Date of Patent: Oct. 6, 2015

(54) PORTABLE ANALYTICAL DEVICE

(75) Inventors: Karl Werner, Wiesloch (DE); Nader Afshar, Fishers, IN (US); Morris J. Young, Indianapolis, IN (US); Alan Greenburg, Indianapolis, IN (US); Paul Galley, Cumberland, IN (US)

(73) Assignee: Roche Diabetes Care, Inc., Indianapolis, IN (US)

( * ) Notice: Subject to any disclaimer, the term of this patent is extended or adjusted under 35 U.S.C. 154(b) by 1825 days.

(21) Appl. No.: 12/158,558

(22) PCT Filed: Dec. 20, 2006

(86) PCT No.: PCT/EP2006/012346

§ 371 (c)(1),
(2), (4) Date: Oct. 17, 2008

(87) PCT Pub. No.: WO2007/076940

PCT Pub. Date: Jul. 12, 2007

(65) Prior Publication Data

US 2009/0304547 A1    Dec. 10, 2009

Related U.S. Application Data

(63) Continuation-in-part of application No. 11/322,542, filed on Dec. 30, 2005, now abandoned.

(60) Provisional application No. 60/743,384, filed on Mar. 1, 2006.

(51) Int. Cl.
*A61B 5/145* (2006.01)
*G01N 33/487* (2006.01)
(Continued)

(52) U.S. Cl.
CPC ...... *A61B 5/14532* (2013.01); *G01N 33/48792* (2013.01); *G06F 19/3406* (2013.01);
(Continued)

(58) Field of Classification Search
CPC .................. A61B 5/14532; A61B 2562/0295;
A61B 5/0002; G01N 33/48792; G06F 19/3406; G06F 19/3456; G06F 19/323
See application file for complete search history.

(56) References Cited

U.S. PATENT DOCUMENTS 5,714,123 A    2/1998   Sohrab
6,494,830 B1   12/2002  Wessel
(Continued)

FOREIGN PATENT DOCUMENTS

EP    1494124       1/2005
EP    1494124 A2    1/2005
(Continued)

OTHER PUBLICATIONS

PCT International Preliminary Report on Patentability for Appln. No. PCT/EP2006/12346 dated Mar. 20, 2007 (10 pages).
(Continued)

*Primary Examiner* — Lore Jarrett
(74) *Attorney, Agent, or Firm* — Barnes & Thornburg LLP

(57) ABSTRACT

A portable analytical device is provided for analysis of a component of a body fluid. A measuring facility within the device may carry out the analysis on a test element inserted therein. The test element may contain a reagent that reacts with a liquid sample of the body fluid when the test element is contacted thereby to produce a change that is characteristic of the analysis. A processor may process measuring values determined by the measuring facility to yield analytical measuring data taking into account calibration values. A standardized, wire-based computer interface may be provided on the analytical device via which the analytical device can be operated by a computer, the analytical measuring data can be transmitted from the analytical device to the computer, the analytical device can be supplied with electrical power by the computer, and the analytical device can provide software to be read-out by the computer.

15 Claims, 3 Drawing Sheets

(51) Int. Cl.
   *A61B 5/00* (2006.01)
   *G06F 19/00* (2011.01)
(52) U.S. Cl.
   CPC ........... *G06F19/3456* (2013.01); *A61B 5/0002* (2013.01); *A61B 2562/0295* (2013.01); *G06F 19/323* (2013.01)

(56) References Cited

U.S. PATENT DOCUMENTS

| | | | |
|---|---|---|---|
| 6,541,266 | B2 | 4/2003 | Modzelewski et al. |
| 6,604,050 | B2 | 8/2003 | Trippel et al. |
| 6,699,188 | B2 | 3/2004 | Wessel |
| 6,743,635 | B2 | 6/2004 | Neel et al. |
| 6,893,545 | B2 | 5/2005 | Gotoh et al. |
| 6,928,311 | B1 | 8/2005 | Pawluczyk et al. |
| 7,267,799 | B1 | 9/2007 | Borich et al. |
| 2002/0162009 | A1 | 10/2002 | Shmueli et al. |
| 2003/0050537 | A1 | 3/2003 | Wessel |
| 2003/0176183 | A1 | 9/2003 | Drucker et al. |
| 2004/0167464 | A1 | 8/2004 | Ireland et al. |
| 2004/0242976 | A1 | 12/2004 | Abreu |
| 2005/0065464 | A1 | 3/2005 | Talbot et al. |
| 2005/0096565 | A1 * | 5/2005 | Chang ........................... 600/584 |
| 2005/0201898 | A1 | 9/2005 | Borich et al. |
| 2006/0248398 | A1 | 11/2006 | Neel et al. |
| 2006/0258215 | A1 | 11/2006 | Lai et al. |

FOREIGN PATENT DOCUMENTS

| | | | |
|---|---|---|---|
| EP | 1764030 | A1 | 3/2007 |
| WO | WO8900024 | | 1/1989 |
| WO | 00/07013 | A2 | 2/2000 |
| WO | WO01/86403 | | 11/2001 |
| WO | WO89/00024 | | 11/2001 |
| WO | WO0186403 | A2 | 11/2001 |
| WO | 02/078512 | A2 | 10/2002 |
| WO | 03/079182 | A2 | 9/2003 |
| WO | WO2004/107977 | | 12/2004 |
| WO | WO2004107977 | A1 | 12/2004 |
| WO | WO2006/102412 | A2 | 9/2006 |
| WO | WO2006/109277 | A2 | 10/2006 |
| WO | 2006/118763 | A2 | 11/2006 |

OTHER PUBLICATIONS

International Search Report based on PCT/EP2006/012346 completed Mar. 20, 2007.
PCT International Preliminary Report on Patentability for Appln. No. PCT/EP2006/012346 dated Mar. 25, 2008.
Microsoft Plug and Play Specification for IEEE 1394, Version 1.Oct.-Mar. 3, 1999 (10 pages).
Microsoft How Plug and Play Works: General, Mar. 28, 2003 (6 pages).
Universal Serial Bus Specification, Revision 1.0, released Jan. 15, 1996 (268 pages).
Notice of Opposition to a European Patent dated Mar. 15, 2012 regarding counterpart European Patent No. EP1 965691, Opponent: Bayer HealthCare LLC (75 pages).
Notice of Opposition to a European Patent dated Mar. 15, 2012 regarding counterpart European Patent No. EP1965691, Opponent: Abbott Diabetes Care Inc. (51 pages).

* cited by examiner

PORTABLE ANALYTICAL DEVICE

CROSS-REFERENCE TO RELATED APPLICATIONS

This application is a U.S. National Stage filing of International Application No. PCT/EP2006/012346, filed Dec. 20, 2006, which claims the benefit of U.S. Provisional Patent Application Ser. No. 60/743,384, filed Mar. 1, 2006, and also of U.S. patent application Ser. No. 11/322,542, filed Dec. 30, 2005, the disclosures of which are all incorporated herein by reference. This application is also a continuation-in-part of U.S. patent application Ser. No. 11/322,542, filed Dec. 30, 2005.

FIELD OF THE INVENTION

The invention relates to a portable, patient-operable electronic analytical device for analysis of a medically significant component of a body fluid for self-monitoring by a patient, in particular a blood glucose measuring device. Analytical devices of this type typically comprise a device housing, a measuring facility arranged inside the device housing for carrying out the analysis on a test element that is inserted through a housing opening into the analytical device and the measuring facility, and a processor with software for processing of the measuring values determined by the measuring facility and for processing the measuring values to yield analytical measuring data taking into account calibration values.

BACKGROUND

For qualitative and quantitative analysis of components of a liquid sample, in particular of a body fluid from humans or animals, test methods working with test elements are used extensively. The test elements generally contain reagents. In order to perform a reaction, the test element is contacted with the liquid sample. The reaction between the liquid sample and the reagent leads to a change in the test element that is characteristic of the analysis, and this change is analyzed using a suitable analytical device. Typically, the analytical device is suitable for analysis of a specific type of test element from a specific manufacturer.

The test elements and the analytical device are mutually adapted components and, in combination, are called an analytical system.

Numerous different types of test elements are known which differ from each other by their measuring principle and the reagents that are used as well as by their structure.

With regard to the measuring principle, calorimetric analytical systems are particularly common. In these systems, the sample reacting with the reagents contained in the test element leads to a color change that can be measured visually or by means of a photometric measuring facility. Moreover, electrochemical analytical systems have gained great significance, in which the sample reacting with the reagents of the test element leads to an electrically detectable change (of an electrical voltage or an electrical current) that is measured with appropriate measuring electronics. Analytical systems of this type are also called amperometric systems.

In many cases, there is a need for regular monitoring of certain analytic blood values. This applies in particular to diabetics who should self-monitor their blood glucose levels frequently in order to maintain these levels within certain nominal limits (ideally, at all times) by suitably adapting their insulin intake via injections or other means to the strongly varying needs. Accordingly, the testing of blood coagulation parameters by patient blood coagulation self-monitoring is also quite common, as is self-monitoring of blood cholesterol levels.

A blood glucose measuring device is a measuring device that can be used for qualitative or quantitative determination of the blood glucose content. For this purpose, it is customary to generate a puncture wound in a body, draw a drop of blood, apply the drop of blood to a test element, and use the test element and the blood glucose measuring device to determine the blood glucose content or concentration of the drop. However, it is also conceivable to measure the blood glucose by means of a continuous measurement, for example with sensors introduced into the body or by a measurement through the skin.

Blood analysis systems should be easy to operate, compact and slim in design, and easy and cheap to manufacture. These practical requirements have led and are leading to the development of blood analysis devices that satisfy these, to some extent contradictory, requirements to the extent possible.

Especially in the area of so-called "home monitoring", i.e. where medical laymen perform simple blood analyses, and, in particular, in the periodical drawing of blood several times daily by diabetics for monitoring of their blood glucose concentration, it is important to have a blood glucose measuring device that is easy and reliable to operate and to have an informative and reliable determination and display of the measuring results.

Conventional analytical devices are so-called stand-alone measuring devices. These devices operate autonomously, self-supporting, and independently. Accordingly, they comprise a display, a measuring facility, a power supply, and a complete user interface that can, for example, comprise a keyboard, a display, a triggering facility or a user guidance. The application purpose and properties of devices of this type are fixed with the exception of occasional adaptation of their firmware.

Approaches to modular concepts aiming to design the application range of these devices more versatile and to make them smaller and cheaper are available.

From document, WO 89/00024, a modular physiological measuring system is known, in which various specific measuring modules, for example an oxygen-measuring module or a blood pressure-measuring module, can be connected to a central unit. Recently, a comparable system for the determination of blood glucose has been developed, in which a blood glucose-measuring module is connected to a PDA.

However, these known systems have been found to be disadvantageous in that the technology of the central unit or PDA is subject to continual technical change by the manufacturers such that, due to non-standardized interfaces between the device and the connected measuring module being used and because of the ongoing changes of the hardware platforms, i.e. the further development of processors and protocols, each and every change made in the device requires that a new application for approval/registration of the measuring module for the medical application at hand had to be filed and be accompanied by proof of the operability of the device in combination with the central unit or PDA.

It is therefore desirable to create an analytical device that is very compact and can be used by an operator in particularly simple fashion.

SUMMARY

The present invention comprises an analytical device and an analytical system with the features of the appended independent patent claims. Preferred embodiments and developments of the invention are evident from the dependent patent claims and the following description and related drawing.

Accordingly, a portable, patient-operable analytical device for analysis of a medically significant component of a body fluid for self-monitoring by a patient, in particular a blood glucose measuring device, with a device housing, a measuring facility arranged inside the housing for carrying out the analysis on a test element that is inserted through a housing opening into the analytical device and the measuring facility, and with a processor with software for processing of the measuring values determined by the measuring facility and for processing the measuring values to yield analytical measuring data taking into account calibration values, may comprise a standardized, wire-based computer interface by means of which the analytical device can be operated by a computer, the analytical measuring data can be transmitted from the analytical device to the computer, and the analytical device can also be supplied with electrical power by the computer.

Since a computer usually has the capability, i.e. the requisite soft- or firmware, to display the data read-out from an analytical device, either through the use of standard software or a specific software adapted to the analytical device and its analytical measuring data, the analytical measuring device does not need to have an intrinsic user interface in preferred embodiments for displaying instructions and/or information for the user for carrying out an analysis such that the display of such instructions and/or information may be implemented exclusively by means of a monitor that is connected to the computer to which the analytical device is connected by means of the interface.

In principle, the computer interface could be implemented in any fashion, i.e. just as well as a wireless interface (e.g. by radio or infrared transmission). However, wireless transmission requires that the analytical device possesses an intrinsic internal or external power supply or is connected to the computer by means of a cable. For this reason, the wire-based computer interface is desirable.

In the case of wire-based data transmission via computer interface, the user of the analytical device must connect the analytical device to the computer. In principle, this is feasible by means of a fitting suitable connection cable. However, in this case the user needs to have at hand a fitting connection cable and to establish the connection in order to facilitate communication of the analytical device and the computer. Especially in the case of manually impaired, ill or visually impaired individuals, this may be difficult. Moreover, the plug connection contacts of the cable may get contaminated or damaged. For this reason, the interface of the analytical device may be provided in the form of a male plug contact attached to the housing of the analytical device which male plug contact can be directly connected to a socket of the computer.

According to an additional embodiment, it is proposed to provide the computer to which the analytical device is connected by means of the interface such as to support visually impaired users of the analytical device. For this purpose, the computer can comprise, for example, a data output with very large characters on a monitor, a data output or data input facility with Braille characters or a speech output facility.

However, the option of displaying the measuring values on a large monitor of a computer instead of the conventional display element that is directly attached to an analytical device and significantly more limited in terms of the space available for display and the display quality, provides a very large display not only for visually impaired users. This is because a user can self-configure the large display very easily and adapt it to his wishes not only with regard to the size of the characters, but also with regard to the quantity and arrangement of the information to be displayed.

The present invention may comprise one or more of the features recited in the attached claims, and/or one or more of the following features and combinations thereof. In one illustrative embodiment, an electronic device for analysis of a body fluid may comprise a housing defining a first opening therein, a measuring facility arranged inside the housing and configured to receive a test element therein via the first opening, at least one electrical circuit arranged inside the housing and a multi-wire connector carried by the housing and electrically connected to the at least one electrical circuit. The measuring facility may be configured to produce measuring values relating to a sample of the body fluid received on the test element. The at least one electrical circuit may be configured to process the measuring values to yield analytical data corresponding to a component of the sample of the body fluid. The multi-wire connector may have at least one wire defining a voltage supply input to the electronic device. The multi-wire connector may be configured to be connected to a mating connector of an external electronic device with the at least one wire configured to receive a supply voltage from the external electronic device.

The measuring facility may comprise at least one electrode configured to produce the measuring values based on an electro-chemical reaction of the body fluid with the test element. Alternatively, the measuring facility may comprise an optical detector configured to produce the measuring values based on at least one optical property resulting from a reaction of the body fluid with the test element. In either case, the measuring facility may be configured to receive therein the test element provided in the form of a test strip having the sample of the body fluid deposited thereon.

Alternatively, the housing may define a second opening extending into the measuring facility and being aligned with the test element when the test element is received in the first opening. In this embodiment, the sample of the body fluid may be received on the test element via the second opening in the housing. The multi-wire connector may be one of a universal serial bus connector and a firewire interface. The electronic device may not include a display, and/or it may not include a user interface for providing user input of instructions or information to the electronic device. The component of the sample of the body fluid may be one of blood glucose, cholesterol and a blood coagulation parameter.

In another illustrative embodiment, an electronic device for analysis of a body fluid may comprise a housing defining a first opening therein, a measuring facility arranged inside the housing and configured to receive a test element therein via the first opening, at least one electrical circuit arranged inside the housing and a multi-wire connector carried by the housing and electrically connected to the at least one electrical circuit. The measuring facility may be configured to produce measuring values relating to a sample of the body fluid received on the test element. The at least one electrical circuit may be configured to process the measuring values to yield analytical data corresponding to a component of the sample of the body fluid. The multi-wire connector may have at least one wire defining a control input to the electronic device and be configured to be connected to a mating connector of an external electronic device with the at least one wire configured to receive control signals from the external electronic device for operating the electronic device.

The measuring facility may comprise at least one electrode configured to produce the measuring values based on an electro-chemical reaction of the body fluid with the test element. Alternatively, the measuring facility may comprise an optical detector configured to produce the measuring values based on at least one optical property resulting from a reaction of the body fluid with the test element. In either case, the measuring facility may be configured to receive therein the test element provided in the form of a test strip having the sample of the body fluid deposited thereon.

Alternatively, the housing may define a second opening extending into the measuring facility and aligned with the test element when the test element is received in the first opening. In this embodiment, the sample of the body fluid may be received on the test element via the second opening in the housing. The multi-wire connector may be one of a universal serial bus connector and a firewire interface. The multi-wire connector may be mounted to, and extend from, the housing. The electronic device may not include a display, and/or it may not include a user interface for providing user input of instructions or information to the electronic device. The component of the sample of the body fluid may be one of blood glucose, cholesterol and a blood coagulation parameter.

In yet another illustrative embodiment, an electronic device for analysis of a body fluid may comprise a housing defining a first opening therein, a measuring facility arranged inside the housing and configured to receive a test element therein via the first opening, at least one electrical circuit arranged inside the housing and a universal serial bus (USB) interface carried by the housing and electrically connected to the at least one electrical circuit. The measuring facility, the at least one electrical circuit and the USB interface may together form a USB device. The measuring facility may be configured to produce measuring values relating to a sample of the body fluid received on the test element. The at least one electrical circuit may be configured to process the measuring values to yield analytical data corresponding to a component of the sample of the body fluid.

The USB interface may be configured to be electrically connected to a mating USB interface of either of a USB host and a USB hub. The USB interface may be a first USB connector configured to be electrically connected to a second USB connector of one of a USB host and a USB hub. The USB host may be one of a personal computer, a laptop computer and a notebook computer. Alternatively, the USB interface may be a wireless USB interface. In any case, the electronic device may not include a display, and/or it may not include a user interface for providing user input of instructions or information to the electronic device. The component of the sample of the body fluid may be one of blood glucose, cholesterol and a blood coagulation parameter. The measuring facility may comprise at least one electrode configured to produce the measuring values based on an electro-chemical reaction of the body fluid with the test element. Alternatively, the measuring facility may comprise an optical detector configured to produce the measuring values based on at least one optical property resulting from a reaction of the body fluid with the test element. The USB interface may be configured to be electrically connected to a mating USB interface of either of a USB host and a USB hub.

In a further illustrative embodiment, an electronic device for analysis of a body fluid may comprise a housing defining a first opening therein, a measuring facility arranged inside the housing and configured to receive a test element therein via the first opening, at least one electrical circuit arranged inside the housing, a memory unit arranged inside the housing and having stored therein instructions for operating the electronic device and an electrical interface electrically connected to the at least one electrical circuit. The measuring facility may be configured to produce measuring values relating to a sample of the body fluid received on the test element. The at least one electrical circuit may be configured to process the measuring values to yield analytical data corresponding to a component of the sample of the body fluid. The electrical interface may be configured for communication with an electrical interface of an external electronic device configured to execute the instructions stored in the memory unit to thereby control the electronic device.

The electronic device may not include a display, and/or it may not include a user interface for providing user input of instructions or information to the electronic device. The component of the sample of the body fluid may be one of blood glucose, cholesterol and a blood coagulation parameter. The measuring facility may comprise at least one electrode configured to produce the measuring values based on an electro-chemical reaction of the body fluid with the test element. Alternatively, the measuring facility may comprise an optical detector configured to produce the measuring values based on at least one optical property resulting from a reaction of the body fluid with the test element.

In still another illustrative embodiment, an electronic device for analysis of a body fluid may comprise a housing defining an opening therein, a measuring facility arranged inside the housing and configured to receive a test element therein via the opening, at least one electrical circuit arranged inside the housing and an interface configured to transfer information between the electronic device and an external electronic device. The measuring facility may be configured to produce measuring values relating to a sample of the body fluid received on the test element. The at least one electrical circuit may be configured to process the measuring values to yield analytical data corresponding to a component of the sample of the body fluid. The electronic device does not include a display.

The electronic device may not include a user interface for providing user input of instructions or information to the electronic device. The component of the sample of the body fluid may be one of blood glucose, cholesterol and a blood coagulation parameter. The measuring facility may comprise at least one electrode configured to produce the measuring values based on an electro-chemical reaction of the body fluid with the test element. Alternatively, the measuring facility may comprise an optical detector configured to produce the measuring values based on at least one optical property resulting from a reaction of the body fluid with the test element.

In still a further illustrative embodiment, an electronic device for analysis of a body fluid may comprise a housing defining an opening therein, a measuring facility arranged inside the housing and configured to receive a test element therein via the opening, at least one electrical circuit arranged inside the housing and an electrical interface configured to transfer information between the electronic device and an external electronic device. The measuring facility may be configured to produce measuring values relating to a sample of the body fluid received on the test element. The at least one electrical circuit may be configured to process the measuring values to yield analytical data corresponding to a component of the sample of the body fluid. The electronic device does not include a user interface for providing user input of instructions or information to the electronic device.

The electronic device may not include a display. The component of the sample of the body fluid may be one of blood glucose, cholesterol and a blood coagulation parameter. The measuring facility may comprise at least one electrode configured to produce the measuring values based on an electro-chemical reaction of the body fluid with the test element. Alternatively, the measuring facility may comprise an optical detector configured to produce the measuring values based on at least one optical property resulting from a reaction of the body fluid with the test element.

In yet another illustrative embodiment, a system for analyzing a body fluid may comprise a body fluid analysis device, an electronic device and an electrical interface configured to transfer information between the body fluid analysis device and the electronic device. The body fluid analysis device may comprising a measuring facility configured to receive a test element therein and configured to produce measuring values relating to a sample of the body fluid received on the test element, and at least one electrical circuit configured to process the measuring values to yield analytical data corresponding to a component of the sample of the body fluid. The electronic device may comprise a processor electrically connected to a display unit. The processor may be configured to receive the analytical data from the body fluid analysis device and to control the display unit to display the analytical data.

The electronic device may include a memory having stored therein instructions for operating the body fluid analysis device. The processor of the electronic device may be configured to execute the instructions stored in the memory to control operation of the body fluid analysis device. Alternatively, the body fluid analysis device may include a memory having stored therein instructions for operating the body fluid analysis device. In this embodiment, the processor of the electronic device may be configured to receive the instructions from the memory of the body fluid analysis device and to execute the instructions to control operation of the body fluid analysis device.

The electrical interface may comprise a first multi-wire connector associated with the body fluid analysis device, and a second multi-wire connector associated with the electronic device. The processor of the electronic device may be configured to automatically control operation of the body fluid analysis device, receive the analytical data from the body fluid analysis device and control the display unit to display the analytical data, upon detection of an electrical connection between the first and second multi-wire connectors. The electrical interface may comprise a universal serial bus interface. In this embodiment, the body fluid analysis device is a USB device and the electronic device is a USB host. The body fluid analysis device may not include a display, and/or it may not include a user interface for providing user input of instructions or information to the electronic device. The component of the sample of the body fluid may be one of blood glucose, cholesterol and a blood coagulation parameter. The electronic device may be one of a personal computer, a laptop computer and a notebook computer. The body fluid analysis device further may comprise a USB connector electrically connected to the at least one electrical circuit, wherein the body fluid analysis device is a USB device and the electronic device is a USB host.

BRIEF DESCRIPTION OF THE DRAWINGS

The invention is illustrated in the following based on an exemplary embodiment that is shown in the figures. The particularities described therein can be used separately or in combination in order to create preferred developments of the invention. In the figures.

DESCRIPTION OF THE ILLUSTRATIVE EMBODIMENTS

Figure 1:
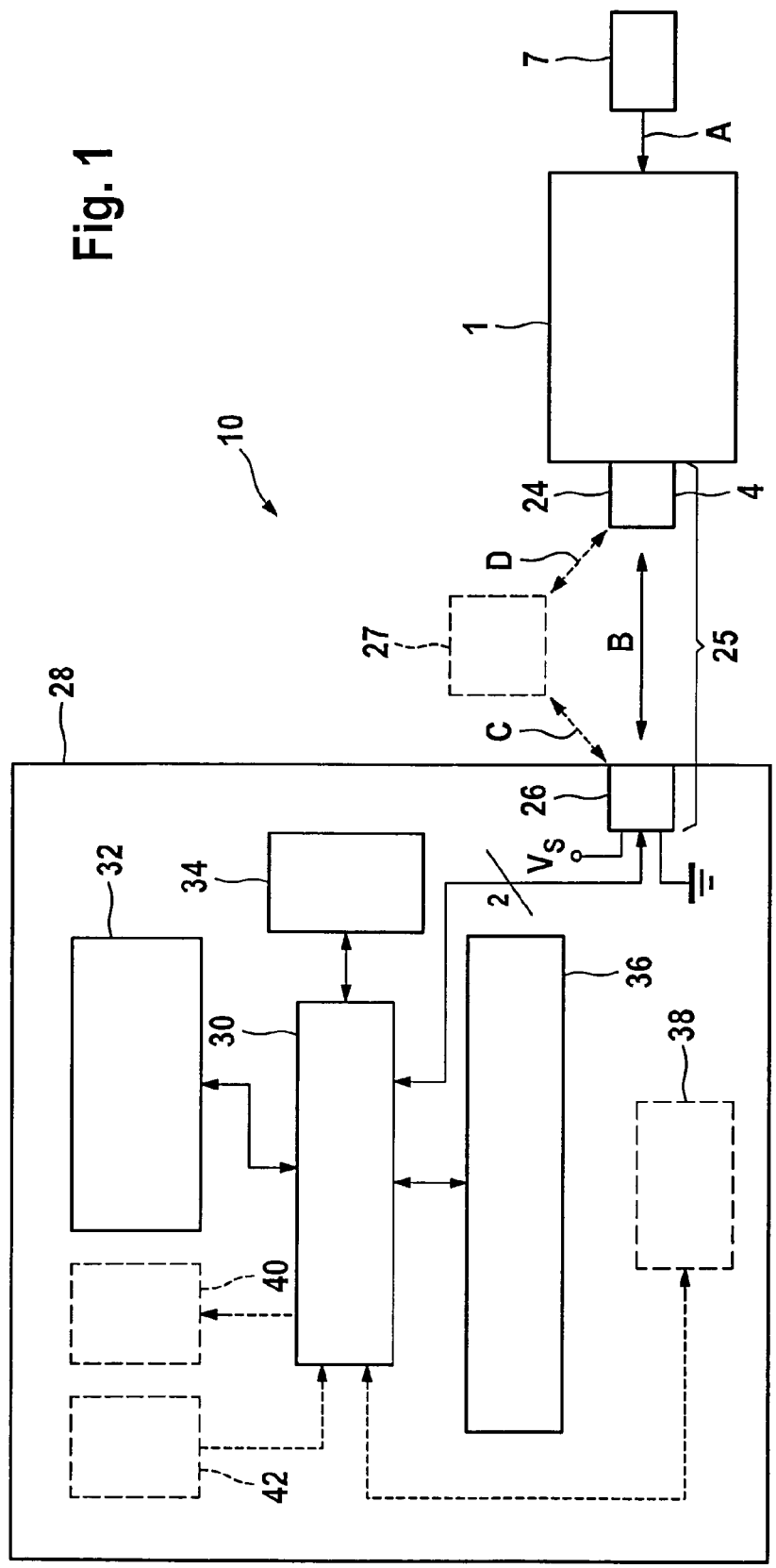
FIG. 1 is a diagram of one illustrative embodiment of a system for analyzing a body fluid.

Referring now to FIG. 1, a diagram of one illustrative embodiment of a system 10 for analyzing a body fluid is shown. In the illustrated embodiment, the system 10 includes an analytical device 1 in the form of a body fluid analysis device that is configured to be electrically connected to an electronic device 28 via an electrical interface indicated generally at 25. The analytical device 1 includes a measuring facility that is configured to receive therein a test element 7, e.g., as illustrated by the directional arrow "A", on which a sample of the body fluid is received. As will be described in greater detail hereinafter with reference to FIG. 3, the measuring facility is generally configured to produce measuring values relating to the sample of body fluid received on the test element 7. The analytical device 1 further includes at least one electrical circuit that is configured to process the measuring values to yield analytical data corresponding to a component of the sample of the body fluid. The analytical device 1 may generally be any electronic device configured to analyze a sample of a body fluid to determine at least one component thereof. Example implementations of the analytical device 1 include, but should not be limited to, a blood glucose measuring device, a body fluid cholesterol measuring device and a blood coagulation parameter measuring device.

The electronic device 28 includes a conventional processor 30 that is electrically connected to a conventional display device or unit 32, a conventional memory device or unit 34, and a conventional keyboard or keypad 36. The electronic device 28 may further include a conventional point and select device 38, one or more conventional speakers 40 and/or a conventional microphone 42, each electrically connected to the processor 30 as shown by dashed-line representation in FIG. 1. The electronic device 28 may generally be any processor-based electronic device, portable or otherwise, that carries its own source of electrical power, e.g., a dedicated voltage source (not shown), and/or that includes a hardwire interface (not shown) configured to be electrically connected to a suitable source of electrical power. Example implementations of the electronic device 28 include, but are not limited to, a conventional personal computer (PC), a conventional laptop or notebook computer, a conventional hand-held electronic device such as a personal data assistant (PDA), or the like.

With any implementation of the analytical device 1 for analyzing body fluids and electronic device 28, an electrical interface 25 is provided to electrically connect the devices 1 and 28. Generally, the electrical interface 25 is a multi-wire, hardwire interface, and in this regard the analytical device 1 includes an electrical connector 24 configured to be electrically connected to another electrical connector 26 of the electronic device 28. In the illustrated embodiment, the electrical connectors 24 and 26 are provided in the form of conventional universal serial bus (USB) connectors, although the electrical interface 25 and electrical connectors 24, 26 may alternatively be configured as a conventional wire-based serial interface, parallel interface, firewire interface or other conventional wire-based electrical interface.

In the specific exemplary embodiment illustrated in FIG. 1, the electrical connector 24 of the analytical device 1 is a male, Type-A USB connector and the electrical connector 26 of the electronic device 28 is a corresponding Type-A USB port. In any case, with the electrical interface 25 implemented in the form of a USB interface, the electronic device 28 acts as a "USB host", and the analytical device 1 as a "USB device", meaning that the electronic device 28 controls operation of the analytical device 1 in accordance with a conventional USB communications protocol carried out over the USB interface 25. The electronic device 28 automatically detects the analytical device 1 when electrical connection is made between the electrical connectors 24 and 26, and if the device 1 has not been connected to the device 28 before, the operating system of the device 28 loads an appropriate driver that is either already resident on the device 28 or is obtained from an external source such as from the device 1 itself. In any case, when the appropriate device driver is loaded onto the electronic device 28, the device 28 then activates the device 1, establishes communication with the device 1 according to a conventional USB communications protocol, and thereafter controls operation of the device 1 via conventional a USB communications protocol. Illustratively, USB communications may be carried according to a conventional USB version 2.0 standard, although other conventional USB protocols may be used. Generally, USB devices are "hot-swappable", meaning that they can be connected and disconnected at any time without having to restart or reboot either device 1 or 28.

In the illustrated embodiment, electrical connection is made between the analytical device 1 and the electronic device 28 by simply inserting male, Type-A USB connector 24 into the Type-A USB port 26 as illustrated by the directional arrow "B". Alternatively, a conventional USB hub 27 may be interposed between the connectors 24 and 26 to allow the electronic device 28 to act as a USB host to multiple USB devices via a the single USB port 26. In this case, the hub 27 includes an electrical connector configured to be electrically connected to the USB port 26 of the electronic device 28, typically via a hardwire cable, as illustrated by the directional arrow "C", and also includes an electrical connector configured to be electrically connected to the electrical connector 24 of the analytical device 1, as illustrated by the direction arrow "D", which may or may not be accomplished via a hardwire cable. Generally, when hardwire cabling is used in a USB interface, the connector/port combination on the host-side is typically a conventional Type-A USB connector/port combination and the connector/port combination on the device-side is a conventional Type-B USB connector. Thus, in cases where a hub 27 is used, the electrical connector on the hub 27 to which the USB port 26 of the electronic device 28 is connected will typically be a conventional Type-B USB connector or port. Likewise, if a hardwire cable is used to connect the device 1 to the hub 27, the electrical connector on the hub 27 to which the USB connector 24 of the device 1 connects will typically be a conventional Type-A port and the electrical connector 24 on the analytical device 1 will typically be a conventional Type-B USB connector or port.

In the illustrated embodiment, the USB connectors 24 and 26 are implemented as "standard" USB connectors, wherein a standard Type-A or Type-B USB connector or port has four connections; one being a voltage bus, one being a ground reference and two forming a pair of differential data connections, D+ and D−, for conducting communications according to a conventional USB communications protocol. Thus, the connectors 24 and 26 each have a voltage bus connection, a ground connection and two data transfer connections. Alternatively, the USB connectors 24 and 26 may be provided in the form of "mini" USB connectors, wherein a mini-USB connector or port has five connections; the four previously described for a standard USB connector and an additional "ID" connection. In either case, the voltage bus of the connector 26 carried by the electronic device 28 is connected to a supply voltage, $V_S$, internal to the electronic device 28. The analytical device 1, in the illustrated embodiment, does not have an internal voltage source or other source of electrical power, and instead the supply voltage, $V_S$, provides the sole source of electrical power for analytical device 1 when electrical connection is made between the devices 1 and 28. In another alternative embodiment, the USB connectors 24 and 26 may be wireless USB connectors, and in this embodiment the analytical device 1 will require a dedicated voltage source such as one or more conventional batteries.

Figure 2:
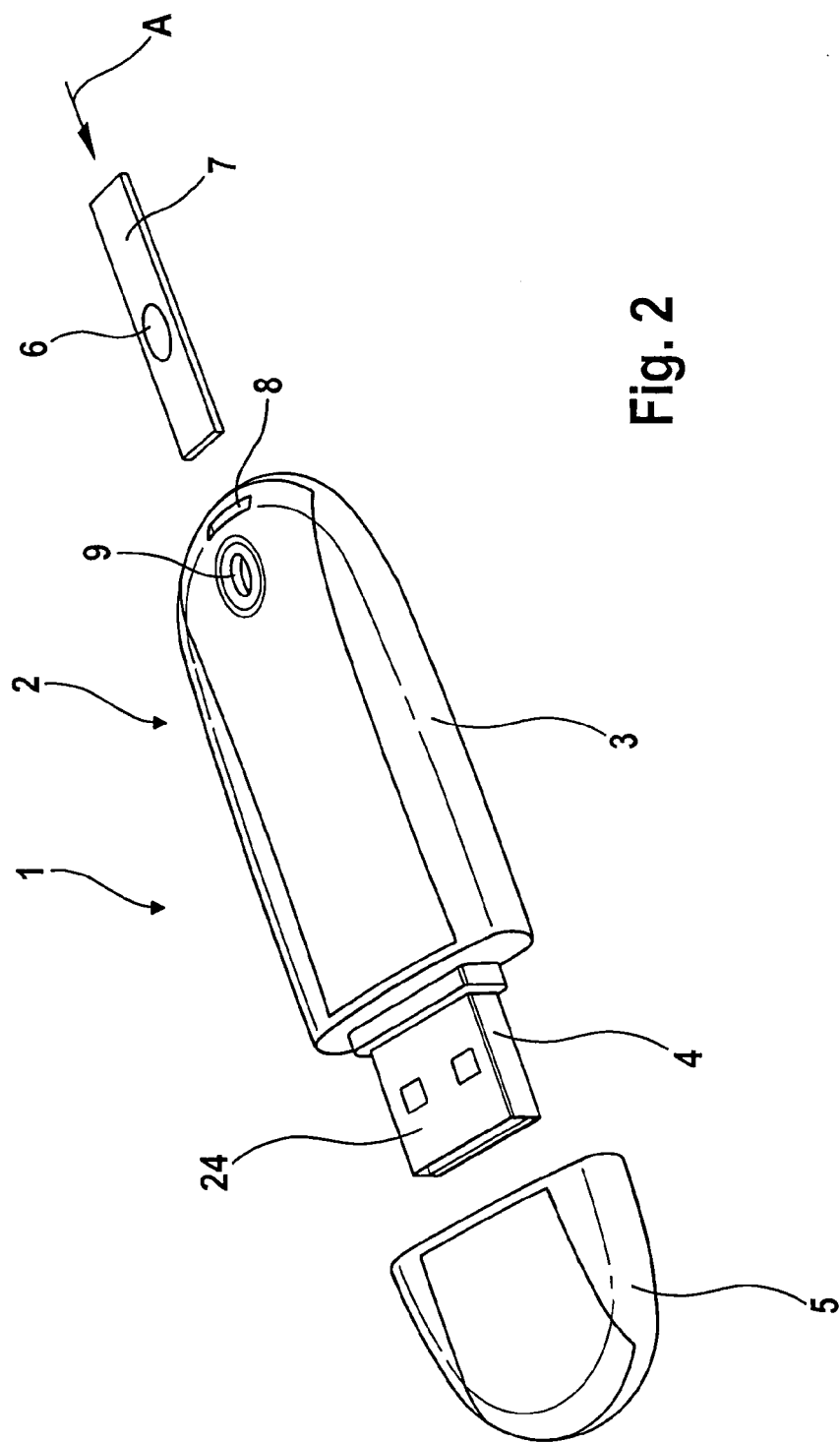
FIG. 2 shows an illustrative embodiment of an analytical device 1 for the analysis of body fluids according to the invention.

Referring now to FIG. 2, an illustrative embodiment of the analytical device 1 of FIG. 1 is shown. The device 1 is generally an electronic device configured to analyze a body fluid, and may illustratively be implemented, as described hereinabove, in the form of a portable, patient-operable blood glucose measuring device for self-monitoring of blood glucose values by the patient. In the illustrated embodiment, the device 1 comprises a housing 3 provided approximately in the design of a conventional USB stick and has a standardized, wire-based USB connector 24 as USB interface 4 that is provided in the form of a male, Type-A USB connector mounted to and extending from the housing 3 of the device 1. A conventional protective cap 5 may be provided to protect the electrical connector 24 from damage during periods of non-use.

One or more components of the body fluid are determined by analyzing a sample of a body fluid of the patient, e.g., blood, which is applied to a test field 6 of the test element 7. The test element 7 is inserted through a slit opening 8 in the housing 3 that leads to a measuring facility arranged in the housing 3, as indicated by the directional arrow A. In one exemplary embodiment, the body fluid is deposited or otherwise received on the test field 6 of the test element 7, and the test element 7 is then inserted, via the opening 8, into the measuring facility arranged in the housing 3. Alternatively, the housing 3 may define a second opening 9 therein that also leads to the measuring facility and that generally aligns with the test field 6 when the test element 7 is inserted, via the opening 8, into the measuring facility arranged in the housing 3. In this embodiment, the test element 7 is first inserted into the measuring facility as just described, and the body fluid is then deposited or otherwise received on the test field 6 via the opening 9.

Numerous different types of test elements 7 are known which differ from each other by their measuring principle and/or reagents that are used, as well as by their structure. With regard to the measuring principle carried out in the measuring facility, any conventional body fluid analytical technique may be used. As one example, optical analytical systems are generally known and commonly used to analyze body fluids, e.g., blood. In these conventional systems, the sample of the body fluid reacting with the reagents contained in the test element 7 produces an optically detectable change that can be measured visually and/or via an optical detection system. Examples of conventional optical analytical systems include, but are not limited to, calorimetric analytical systems, wherein the body fluid sample reacting with the reagents contained in the test element 7 leads to a color change that can be measured visually or by means of a conventional photometric measuring facility, reflectance-type analytical systems wherein the body fluid sample reacting with the reagents contained in the test element 7 leads to changes in the reflectance properties of the sample that can be measured by a conventional reflectance measuring facility, and fluorescence or phosphorescence-type analytical systems wherein the body fluid sample reacting with the reagents contained in the test element is illuminated which leads to a resulting visible emission that can be measured by a suitable conventional fluorescence or phosphorescence measuring facility.

Moreover, electrochemical analytical systems are also known, and in such systems the body fluid sample reacting with the reagents of the test element 7 leads to an electrically detectable change (e.g., of an electrical voltage or an electrical current) that is measured with appropriate conventional measuring electronics including, for example, one or more conductive electrodes. Analytical systems of this type are generally called amperometric systems. The measuring facility contained in the housing 3 may, for example, be a colorimetric or electrochemical measuring facility, and in any case the measuring facility is configured to produce measuring values relating to the sample of the body fluid received on the test element 7.

An electronic analytical device 1 of the type shown in FIG. 2 is, for example, a blood glucose meter 2, a cholesterol measuring device or a blood coagulation parameter measuring device. The analytical device 1 shown in FIG. 2 is a portable, patient-operable blood glucose measuring device 2 for self-monitoring of blood glucose values by the patient. It comprises a housing 3 provided approximately in the design of an USB stick and has a standardized, wire-based USB interface 4 that is provided in the form of a male plug contact on the housing 3 of the analytical device 1. The plug contact of the USB interface 4 can be covered by a protective cap 5.

A measuring facility for carrying out a blood glucose determination is arranged in the housing 3 of the blood glucose measuring device 2. The blood glucose values are determined by means of a drop of the patient's blood, which is then applied to a test field 6 of a test element 7. The test element 7 can be inserted through a slit 8 in the housing 3 into the blood glucose measuring device 2 and the measuring facility situated therein by means of a motion indicated by the direction of the arrow. A measuring facility of this type can, for example, be a calorimetric or electrochemical measuring facility. In other embodiments, the test elements 7 are situated in the housing 3, for example in the form of cartridges, and are wetted by the drop of blood through an opening 9 in the housing 3.

A blood glucose measuring device 2 carries out the blood glucose determination by means of a processor and transmits the analytical measuring data thus determined via the USB interface 4 to a computer.

In order to connect the analytical device 1 to a computer (not shown in FIG. 2) by means of the USB interface 4, the USB plug of the analytical device 1 is plugged into the corresponding USB socket of the computer. By this means, it is feasible to transmit data from the analytical device 1 to the computer in order to display operating parameters or analytical measuring data of the analytical device 1 by means of the computer. Moreover, it is also feasible to transmit data from the computer to the analytical device 1 via the USB interface 4 such that the analytical device 1 can be operated by means of the computer, for example in order to configure the analytical device 1 or to trigger certain actions of the analytical device 1, in particular the carrying out of an analysis with a test element 7 that is inserted into the analytical device 1. Illustratively, the analytical device 1 can be fully or nearly fully operated by means of the computer.

A wire-based computer interface of the computer can, for example, be a serial interface, a parallel interface, a firewire interface or, illustratively, a USB interface 4. The USB interface 4 is desirable since it is very common, requires little space, and facilitates rapid data transmission.

Illustratively, the blood glucose measuring device 2 does not comprise an intrinsic user interface for operating the blood glucose measuring device 2 such that the operation of the blood glucose measuring device 2 for carrying out an analysis on a test element 7 that is inserted into the blood glucose measuring device 2 is implemented exclusively by the computer to which the blood glucose measuring device 2 is connected by means of the USB interface 4, for example by the keyboard of the computer, and thus without input elements on the blood glucose measuring device 2.

Illustrative embodiments dispense altogether with a user interface for operating the blood glucose measuring device 2, for example dispense with a keyboard. In this case, the computer to which the blood glucose measuring device 2 is connected recognizes when a test element 7 is being inserted into the blood glucose measuring device 2 and automatically starts-up the measurement and the display of the measuring result, for example on the monitor of the computer without this requiring an input of the user on a user interface.

Moreover, the blood glucose measuring device 2 does not comprise an intrinsic user interface for displaying analytical measuring data that was determined in an analysis by the blood glucose measuring device 2 such that the display of the analytical measuring data determined in an analysis is implemented exclusively by the computer to which the blood glucose measuring device 2 is connected by means of the USB interface 4, for example by a monitor of the computer.

The computer to which the blood glucose measuring device 2 is connected can be used also for documenting other self-monitoring data of the user which the computer reads-out from the blood glucose measuring device 2 or which are entered by the user. Self-monitoring data of this type can be relevant data for the monitoring, diagnosis or therapy of the blood glucose disease, such as type, time, and quantity of meals ingested, physical activities, insulin quantities administered or other relevant events.

In order for the history of his data to be available to the user of the analytical device 1, even when it is connected to other or various computers, it can be desirable for the analytical device 1 to comprise a measuring value memory in which the computer can store measuring values and, if applicable, times (date and time of day of the measurement) or calibration data. This allows the user to connect the analytical device 1 to other computers and read-out, display or analyze his previous measuring values.

In some embodiments, the analytical device 1 does not comprise an intrinsic or integrated power supply such that it is supplied with power exclusively by the computer to which it is connected by means of the USB interface 4.

Upon connecting the analytical device 1 to the computer by means of the USB interface 4, the computer automatically recognizes the newly connected hardware and loads the necessary pre-installed drivers and application programs for read-out of the data from the analytical device 1 and for operation of the analytical device 1 by the computer. In order to render the analytical device 1 universally operable, i.e. without pre-configuration of the corresponding computer, and thus provide for its use on any computer, an additional embodiment can provide the analytical device 1 to comprise a memory in which the software required for operation of the analytical device 1 is stored, and can provide this software to be read-out by the computer via the interface of the analytical device 1 when the analytical device 1 becomes connected to a computer.

However, in other embodiments it can also be desirable not to require any specific drivers and/or specific software and for the analytical device 1 to be read-out with standard software, for example a browser such as Windows Explorer, which is customarily installed on a computer. In this case, the analytical device can be operated very universally on the majority of computers without any need for pre-configuration of the computer.

Figure 3:
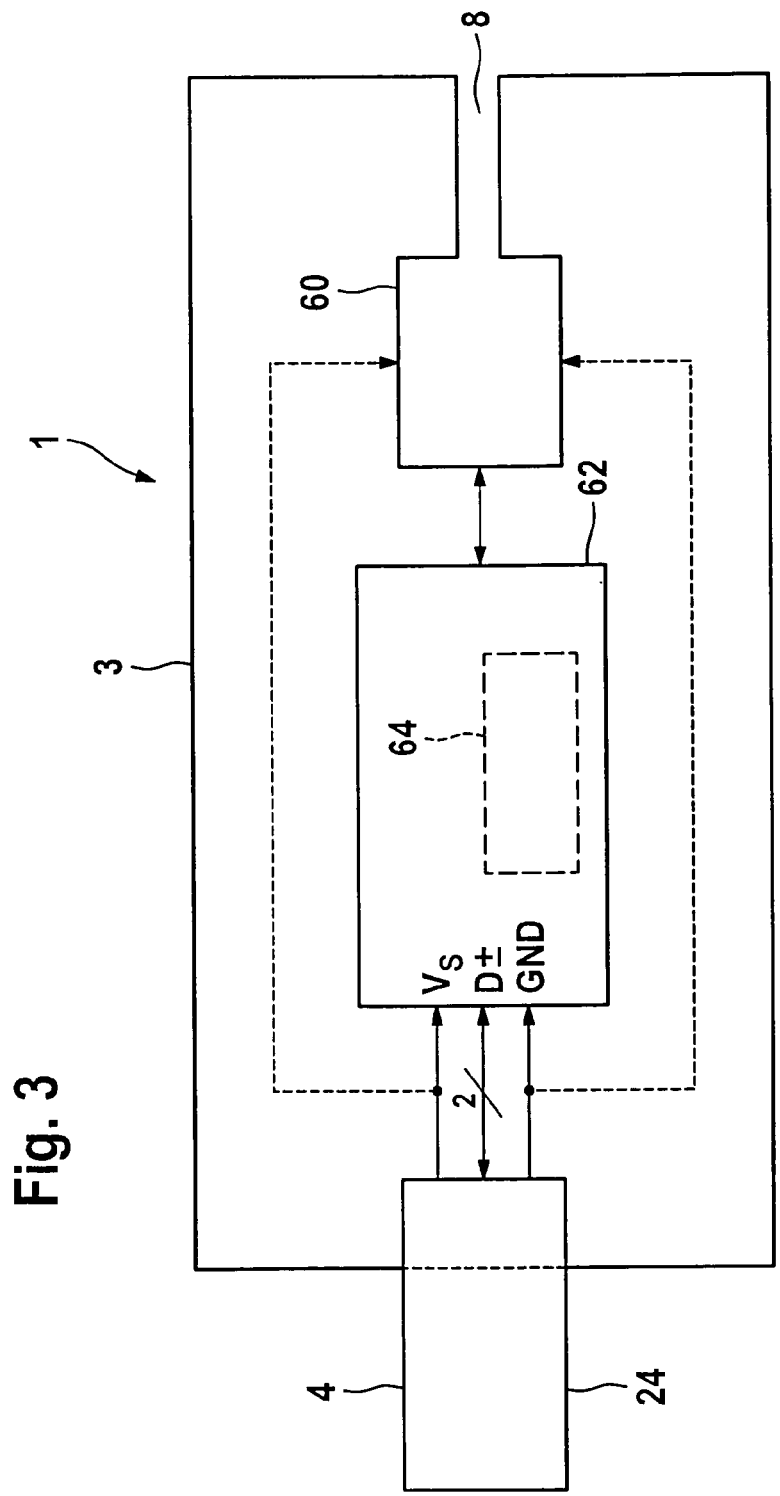
FIG. 3 is a schematic diagram of one illustrative embodiment of the analytical device 1 illustrated in FIG. 2.

Referring now to FIG. 3, a schematic diagram of one illustrative embodiment of the analytical device 1 of FIG. 2 is shown. In the illustrated embodiment, which is generally representative of a cross-sectional view along a longitudinal axis of the device 1, the opening or slit 8 in the housing 3 is shown leading to a measuring facility 60 which may be implemented in any of the forms described hereinabove. The measuring facility 60 is electrically connected to conventional signal processing circuitry 62 which is, in turn, electrically connected to the electrical connector 24. The voltage supply line and the ground reference line of the connector 24 are electrically connected to supply voltage and ground reference inputs, $V_S$ and GND respectively, of the signal processing circuitry 62. The communication lines, e.g., D+ and D−, of the electrical connector 24 are likewise electrically connected to the signal processing circuitry 62.

In embodiments where the measuring facility 60 includes one or more electrical components requiring a supply voltage for operation, the voltage supply line and the ground reference line of the electrical connector 24 are also electrically connected to the measuring facility as shown by dashed line representation in FIG. 3. As discussed hereinabove, the analytical device 1 does not include a voltage supply, and any electrical power required for operation of the device 1 is supplied by the electronic device 28 via the electrical interface 25. In particular, the multi-wire electrical connector 24 has at least one wire that defines a voltage supply input to the analytical device 1, and the electrical connector 24 configured to be connected to a mating connector 26 of the external electronic device 28 with the at least one wire making electrical contact with the voltage supply line, $V_S$, of the electrical connector 26 so as to receive the supply voltage from the electronic device 28.

The signal processing circuitry 62 includes at least one electrical circuit that is arranged inside the housing 3 and configured to process the measuring values produced by the measuring facility 60 in a conventional manner to yield analytical data corresponding to a component, e.g., blood glucose concentration, of the sample of the body fluid received on the test element 7. The analytical data is then provided by the signal processing circuitry 62 to the electronic device 28 via the electrical interface 25 as shown and described with respect to FIG. 1. In embodiments of the system 10 wherein the electrical interface 25 is a USB interface as described in detail hereinabove, the signal processing circuitry 62 will typically, although not necessarily, include a conventional processor circuit, such as a microprocessor. Such a processor is configured to process the measuring values produced by the measuring facility 60 to yield the analytical data, to also communicate with the processor 30 of the electronic device 28 via the USB interface 25 in accordance with a conventional USB communications protocol, and to act upon instructions received from the processor 30.

In other embodiments, the signal processing circuitry 62 may or may not include a conventional processor circuit, but will in any case include appropriate circuitry configured to process the measuring values produced by the measuring facility 60 and to act upon instructions provided by the processor 30 of the electronic device 28. In any case, the multi-wire electrical connector 24 carried by the housing 3 and electrically connected to the signal processing circuitry 62, has at least one wire (two shown in FIGS. 1 and 3) defining a control input to the analytical device 1. When the multi-wire electrical connector 24 is connected to the mating connector 26 of the electronic device 28 to establish the electrical interface 25, the control input to the analytical device 1 is electrically connected to the processor 30 and may receive control signals from the processor 30 of the electronic device 28 for operating the analytical device 1.

The signal processing circuitry 62 may, in some embodiments, include a memory unit 64 arranged inside the housing 3, and the memory unit 64 may have stored therein instructions for operating the analytical device 1. In such embodiments, the signal processing circuitry 62 may include a processor configured to execute the instructions stored in the memory unit 64 to operate the analytical device 1 as described herein. Alternatively, the processor 30 of the electronic device 28 may, after the electrical interface 25 is established between the devices 1 and 28, retrieve the instructions from the memory unit 64 and execute the instructions to operate and control the analytical device 1 as described herein.

With the system 10 illustrated and described herein, data may generally be provided from the analytical device 1 to the electronic device 28 via the electrical interface 25, and the processor 30 of the electronic device 28 may be configured to process such data and control the display unit 32 to display operating parameters and/or analytical data provided by the analytical device 1. Likewise, data in the form of instructions or control signals may be provided by the processor 30 of the electronic device 28 to the analytical device 1 via the electrical interface 25 such that the processor 30 of the electronic device 28 can control operation of the analytical device 1, for example in order to configure the analytical device 1 and/or to trigger certain actions of the analytical device 1, in particular the carrying out of an analysis of a test element 7 that is inserted into the device 1. In this manner, the analytical device 1 can be partially or fully controlled and operated by the processor 30 of the electronic device 28.

In the exemplary embodiments illustrated and described herein, it will be noted that the analytical device 1 does not include an intrinsic user interface for providing user input of instructions or information to the analytical device 1 such as for operating the device 1. Rather, operation of the analytical device 1 in carrying out an analysis on a test element 7 that is inserted into the device 1 is controlled exclusively by the electronic device 28. For example, the processor 30 of the electronic device 28 may illustratively be programmed to recognize, after the electronic device 28 is electrically connected to the analytical device 1 via the electrical interface 25, when a test element 7 is being inserted into the device 1, and to then automatically command start-up of the measurement and the display of the measuring result, for example, on the display unit 32 of the computer without this requiring an input of the user on any user interface. In such embodiments, the system 10 may dispense altogether with any type of user interface for controlling and operating the device 1. In alternative embodiments, any user input that may be required or that may be useful to the operation of the device 1 may be entered by the user via the keyboard or keypad 36 and/or point and select device 38, or alternatively via a microphone 42 in embodiments of the electronic device 28 that are configured to receive and act upon voice commands from the user.

In the exemplary embodiments illustrated and described herein, it will be further be noted that the analytical device 1 does not include an intrinsic user interface for displaying or otherwise conveying analytical data determined by the device 1. Rather, display or other conveyance of analytical data determined by the analytical device 1 is carried out exclusively by the electronic device 28. For example, the processor 30 of the electronic device 28 may illustratively be programmed to receive via the electrical interface 25 analytical data from the analytical device 1 resulting from analysis of a sample of body fluid received on a test element 7, and to present this analytical data to the patient using only data presenting components of the electronic device 28. In one embodiment, for example, the processor 30 may control the display unit 32 to display thereon the analytical data in textual and/or graphic form. Alternatively or additionally, the processor 30 may control the speaker 40, in embodiments of the electronic device 28 that include a speaker 40, to audibly convey the analytical data to the patient.

The electronic device 28 to which the analytical device 1 is connected may also be used also for documenting other self-monitoring data of the patient which the electronic device 28 may import from the analytical device 1 and/or which may be entered into the electronic device 28 by the patient. Self-monitoring data of this type can be relevant, for example, for the monitoring, diagnosis or therapy of the blood glucose disease, such as type, time, and quantity of meals ingested, physical activities, insulin quantities administered and/or other relevant events.

In order for the history of such data to be available to the user of the analytical device 1, particularly when the device 1 may be connectable to multiple different electronic devices, it may be desirable to include the memory unit 64 in signal processing circuitry 62. In such cases, the processor of any electronic device that the analytical device 1 may electrically connect to can then be configured to store analytical data, calibration data and/or other data (e.g., date and time of day of the measurement) in the memory unit 64 of the analytical device 1. This allows the user to connect the analytical device 1 to more than one electronic device for the purpose of importing, displaying and/or analyzing any one or more of the stored analytical data values.

As described hereinabove, the processor 30 of the electronic device 28 operates to automatically recognize the analytical device 1 when it is connected to the electronic device 28 via a USB interface 25. The processor 30 then loads the necessary pre-installed drivers and application programs for importing data from the device 1 and for controlling operation of the device 1 by the electronic device 28. In order to render the analytical device 1 universally operable, i.e., without pre-configuration of the corresponding electronic device 28, and thus provide for its use with any electronic device 28, the signal processing circuitry 62 of the device 1 may include the memory unit 62 having stored therein instructions in the form of software required for controlling operation of the device 1. In this embodiment, the processor 30 of any electronic device 28 to which the analytical device 1 is connected may be operable to import this software from the memory unit 64 and then execute the imported software to control operation of the device 1.

However, in other embodiments it may be desirable not to require any specific drivers and/or specific software for controlled operation of the analytical device 1, and for the analytical data determined by the device 1 to instead be imported from the device 1 by the electronic device 28 using standard software, for example a browser such as Windows Explorer or Microsoft Internet Explorer, which may be previously installed on the electronic device 28, such as when the electronic device 28 is implemented in the form of a PC, laptop or notebook computer. In this case, the analytical device 1 can be operated universally by the majority of computers without any need for pre-configuration of the computer.

While the invention has been illustrated and described in detail in the foregoing drawings and description, the same is to be considered as illustrative and not restrictive in character, it being understood that only illustrative embodiments thereof have been shown and described and that all changes and modifications that come within the spirit of the invention are desired to be protected.

LIST OF REFERENCE NUMBERS 1 analytical device
2 blood glucose measuring device
3 housing
4 USB interface
5 protective cap
6 test field
7 test element
8 slit
9 opening
10 system
24 electrical connector of 1
25 electrical interface
26 electrical connector of 28
27 hub
28 electronic device
30 processor
32 display
34 memory
36 keyboard
60 measuring facility
62 signal processing circuitry
64 memory
A arrow (7-1)
B arrow (24-26)
C arrow (27-26)
D arrow (27-24)
$V_S$ supply voltage
GND ground
D+ communication line
D− communication line

The invention claimed is:

1. A portable, patient-operable analytical device for analysis of a medically significant component of a body fluid for self-monitoring by a patient, comprising:
a device housing defining an opening therein,
a measuring facility arranged inside the device housing and configured to receive a test element that is inserted through the housing opening into the measuring facility, the measuring facility configured to analyze one of an optical and electrochemical change in a received test element upon which a liquid sample of the body fluid has been deposited and to generate measuring values resulting from the analysis,
a processor arranged inside the device housing and including a memory having software stored therein, the processor configured to execute at least a portion of the software to process the measuring values to yield analytical measuring data taking into account calibration values, and
an electrical connector carried by the housing and electrically connected to the processor, the electrical connector configured to operatively connect to an external electronic device, the electrical connector configured to transmit the analytical measuring data from the analytical device to the external electronic device, the electrical connector comprising a voltage supply input configured to transmit an external supply of electrical power to the analytical device from the external electronic device, wherein the analytical device is further configured to provide one or more portions of the software through the electrical connector to the external electronic device when the electrical connector is operatively connected to the external electronic device.

2. The analytical device of claim 1, wherein the measuring facility is configured to analyze an electrochemical change in the received test element, the measuring facility comprising measuring electronics comprising at least one electrode configured to produce the measuring values based on an electrochemical reaction between the liquid sample and a reagent in the test element.

3. The analytical device of claim 2 wherein the electrochemical reaction between the liquid sample and the reagent in the test element results in a change of one of a voltage signal and a current signal that is measured by the measuring electronics and the detectable electrochemical change is one of voltage and current respectively.

4. The analytical device of claim 1 wherein the measuring facility is configured to analyze an optical change in the received test element, the measuring facility comprising a photometric measuring facility, and wherein the photometric measuring facility comprises an optical detector configured to produce the measuring values based on at least one optical property resulting from a reaction between the liquid sample and a reagent in the test element.

5. The analytical device of claim 4 wherein the reaction between the liquid sample and the reagent in the test element results in a color change of the test element such that the at least one optical property includes color and the optically detectable change is the color change.

6. The analytical device of claim 1 wherein operation of the analytical device is controlled by the external electronic device via a USB communications protocol when the electrical connector is operatively connected to the external electronic device.

7. The analytical device of claim 1 wherein the electrical connector comprises a multi-wire connector.

8. The analytical device of claim 1 wherein the electrical connector comprises a male plug contact attached on the housing of the analytical device.

9. The analytical device of claim 1 wherein the measuring facility comprises one of a colorimetric measuring facility wherein the one of the optical and electrochemical change in the received element is an optically detectable change and an electrochemical measuring facility wherein the one of the optical and electrochemical change in the received element is a detectable electrochemical change.

10. The analytical device of claim 1 wherein the analytical device comprises one of a blood glucose meter, a cholesterol measuring device and a blood coagulation parameter measuring device.

11. A portable, patient-operable analytical device for analysis of a medically significant component of a body fluid for self-monitoring by a patient, comprising:
a device housing defining an opening therein,
a measuring facility arranged inside the device housing configured to receive a test element via the housing opening and configured to analyze one of an optical and electrochemical change in the test element upon which a liquid sample of the body fluid is deposited and generating measuring values resulting from the analysis,
a processor arranged inside the device housing and including a memory having stored therein software at least a portion of which is executable by the processor to process the measuring values to produce analytical measuring data taking into account calibration values, and
an electrical connector having one end attached to the housing and electrically connected to the processor and having an opposite end extending from the device housing, the opposite end of the electrical connector receiving electrical power to operate the processor and the measuring facility from an external device connectable to the electrical connector.

12. The analytical device of claim 11 wherein the processor provides one or more portions of the software via the electrical connector to the external device when the external device is connected to the analytical device via the electrical connector.

13. A system for analyzing a medically significant component of a body fluid for self-monitoring by a patient, comprising:
an electronic device comprising a display, a first electrical connector and a first processor electrically connected to the display and the first electrical connector, and an analytical system comprising:
a device housing defining an opening therein,
a test element comprising a reagent configured to react with a body fluid to generate a detectable change, the test element being insertable through the opening,
a measuring facility arranged inside the device housing and configured to receive the test element via the opening, the measuring facility configured to analyze the detectable change in the test element having a liquid sample of the body fluid received thereon and to generate measuring values resulting from the analysis,
a second processor arranged inside the device housing and including a memory having stored therein software at least a portion of which is executable by the at least one of the first and second processors to process the measuring values to produce analytical measuring data, and
a second electrical connector carried by the device housing and electrically connected to the second processor,
wherein the first and second electrical connectors are configured to be directly connected to each other to define an operative connection between the first and second processors, the operative connection comprising a data connection through which the analytical measuring data is provided from the second processor to the first processor and through which controlling signals are exchanged between the first and second processors to control the display to convey the analytical measuring data display in at least one of a textual and a graphic form,
wherein the first processor is configured to one of control operation of the analytical device via the operative connection and trigger actions of the analytical device via the operative connection to analyze the detectable change in the test element inserted into the measuring facility and having the liquid sample of the body fluid received thereon.

14. The analytical device of claim 13 wherein the electronic device comprises at least one of a keyboard, a point and select device and a microphone,
and wherein the first processor is configured to control the display to display user input instructions and/or information relating to the analysis,
and wherein user input required in response to the user input instructions and/or information is provided by the user via the at least one of the keyboard, the point and select device and the microphone.

15. The analytical device of claim 13 wherein the electronic device comprises a speaker operatively connected to the first processor, and wherein the first processor is configured to control the speaker to display the analytical measuring data by audibly conveying the analytical measuring data.

* * * * *